United States Patent [19]

Takamizawa et al.

[11] 4,042,613

[45] Aug. 16, 1977

[54] BENZOPHENONE DERIVATIVES AND THEIR PREPARATION AND APPLICATION

[75] Inventors: Minoru Takamizawa; Yasushi Yamamoto; Yoshio Inoue, all of Annaka; Atsumi Noshiro, Chiba; Hitoshi Fujii, Tokyo, all of Japan

[73] Assignees: Dai Nippon Printing Co., Ltd.; Shin-Etsu Chemical Co., Ltd., both of Tokyo, Japan

[21] Appl. No.: 569,756

[22] Filed: Apr. 21, 1975

[30] Foreign Application Priority Data

Apr. 23, 1974 Japan .................................. 49-45711
July 31, 1974 Japan .................................. 49-87612

[51] Int. Cl.² ............................................... C07F 7/08
[52] U.S. Cl. .............................. 260/448.2 B; 96/35.1; 96/33; 96/88; 101/456; 101/463; 260/448.2 E; 427/259
[58] Field of Search ................................ 260/448.2 B

[56] References Cited

U.S. PATENT DOCUMENTS

| | | | |
|---|---|---|---|
| 2,591,736 | 4/1952 | Sommer | 260/448.2 B |
| 2,938,047 | 5/1960 | Black | 260/448.2 B |
| 3,489,781 | 1/1970 | Wilkus et al. | 260/448.2 B |
| 3,715,370 | 2/1973 | Wilkus et al. | 260/448.2 B X |

*Primary Examiner*—Paul F. Shaver
*Attorney, Agent, or Firm*—Toren, McGeady and Stanger

[57] ABSTRACT

Novel benzophenone derivatives represented by the general formula $R_m^1-C_6H_{5-m}-CO-C_6H_{5-n}-R_n^2$ where $R^1$ is a halogen atom, a monovalent $C_{1-10}$ hydrocarbon, alkoxy, thioalkoxy, amino, or dialkylamino group, $R^2$ is an unsubstituted or organosiloxy-substituted organosilyl group, and $m$ and $n$ are each integers from 1 to 5. The benzophenone derivatives are useful as photosensitizers for making photo-curable compositions by blending with photo polymerizable resins, especially photopolymerizable organosilicon resins. Such photo-curable organosilicon resin compositions are further useful for making dry-planographic printing plates comprising non-image areas formed from the polymerized and cured layers of the composition.

32 Claims, 4 Drawing Figures

BENZOPHENONE DERIVATIVES AND THEIR PREPARATION AND APPLICATION

FIELD OF THE INVENTION

This invention relates to novel benzophenone derivatives useful as photosensitizers and their preparation and application.

DESCRIPTION OF THE PRIOR ART

Many photosensitizers have been developed and proposed many for accelerating the polymerization of a photopolymerizable resin. In this sense, the photosensitizer is a substance that can absorb the energy of light, and thus becomes excited and capable of giving energy to the resins and accelerating the polymerization, when the excited electrons therein collide with the molecules of the resins. For the purpose, the photosensitizers are required to possess an excellent capability for photosensitization and other properties including, for example, sufficient compatibility with the photopolymerizable resins. If a photosensitizer is not sufficiently compatible with the photopolymerizable resin, it tends to become separated and isolated from the resin and exhibit a poor photosensitization, resulting in the non-uniform polymerization of the resin and the unsatisfactory formation of cured films. Further, photocurable compositions containing such photosensitizers are not suitable for storage for a long period of time.

Various photocurable compositions have been developed for use in the making of dry-planographic printing plates, but satisfactory results have not been obtained.

Generally speaking, the printing plates used in planographic printing, unlike those used in letter-press or gravure printing, have no areas either raised above or depressed below the surface to define the image areas, the image and non-image areas lying substantially printing plates operates on the principle that printing plates is worked, based on the fact that water and oil are immiscible, by first making the nonimage areas water-receptive through chemical or mechanical treatment while the image areas are made oil-receptive by the transfer of oleophilic resins or with a photoprocess, then dampening the plate with a fountain solution so that the water-receptive non-image areas become dampened, and then allowing ink to transfer to the plate so that the ink coats the oil-receptive image areas and not the dampened non-image areas, followed finally by transferring the ink on the image areas to a copy sheet, to produce printed matter.

The above printing method is disadvantageous, for example, because the dampening solution tends to transfer to the surface of the ink roller on the press during a printing run, causing emulsification of the ink and soiling of the copy sheet surfaces, and causing curling and change in dimensions of the printed sheets. These disadvantages are particularly significant in the process color printing, in which the printed images do not come out with sufficient sharpness. Further, in planographic printing, it is extremely difficult to properly control the balance quantitywise between the ink and the dampening solution, which is required to secure image fidelity and uniformity and thus the irregularity in color tone of the colored print is difficult to prevent.

For the purpose of overcoming the above-described disadvantages and difficulties, attempts have been made to develop dry-planography in which no dampening solution is used. For example, a proposal has been made to provide a dry-planographic printing plate comprising a base plate or substrate of aluminum having one surface with ink-receptive areas composed of layers of a diazo-type photosensitive composition and a dimethylpolysiloxane rubber and a positive transparency or pattern laid thereon, expose this base plate to light from above to insolubilize the diazo composition thereby to give a latent image. The diazo layer on the unexposed areas is removed by development and finally the layer of the dimethylpolysiloxane gum on the unexposed areas is stripped off to bare the underlying metal surface (see British Patent Specification 1,146,618). Another proposal is to provide a dry-planographic printing plate prepared by continuously coating the surface of an aluminum base plate with a photosensitive diazo layer, an adhesive layer and a silicone rubber layer successively, and exposing the thus coated base plate to light through a negative pattern laid thereon, followed by development by photodecomposition of the photosensitive layer and stripping of the silicone gum layer on the exposed areas, to obtain the desired printing plate (see U.S. Pat. No. 3,511,178).

In the above prior art, the presence of a nonphotosensitive silicone gum layer between the diazo photosensitive layer and the positive or negative pattern makes it difficult to reproduce the images on the positive or negative pattern with fidelity and uniformity. Furthermore, the removal or stripping off of the silicone gum layer from the underlying plate surface which is conducted depending on the changes in the solubility in solvent of the photosensitive layer, disadvantageously, causes the resulting images to have their edges lacking in sharpness. Further disadvantages of the prior art manufacture of such dry-planographic printing plates may be attributed to the complicated processes including the steps of successive formation of two or three layers on the surface of the base plate, exposure to light, and development.

OBJECTS OF THE INVENTION

It is an object of this invention to provide novel benzophenone derivatives and their preparation.

It is another object of the invention to provide photosensitizers consisting essentially of the benzophenone derivatives.

It is a further object of the invention to provide photocurable compositions consisting essentially of the benzophenone derivatives and one or more photopolymerizable resins, especially photopolymerizable organosilicon resins.

It is a still further object of the invention to provide dry-planographic printing plates comprising a base plate having non-image areas composed of a polymerized and cured layer of a photopolymerizable composition, comprising a photopolymerizable organosilicon resin.

DETAILED DESCRIPTION OF THE INVENTION

Figure 1:
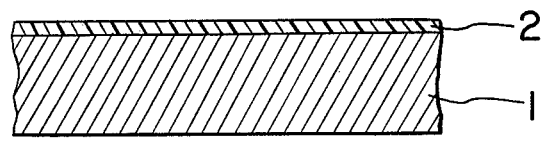
FIG. 1 represents a sectional view of a dry-planographic printing plate showing the base and an overlying layer of the composition, comprising a photopolymerizable organosilicon resin.

The benzophenone derivative of this invention is represented by the general formula

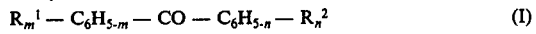

where $R^1$ is a halogen atom, a monovalent $C_{1-10}$ hydrocarbon group, an alkoxy group, a thioalkoxy group, an amino group, or a dialkylamino group, $R^2$ is an unsubstituted or organosiloxy-substituted organosilyl group, and each of $m$ and $n$ is an integer of from 1 to 5.

Now, referring to the description of Formula I above, the halogen atoms denoted by $R^1$ are exemplified by chlorine and bromine; the monovalent $C_{1-10}$ hydrocarbon groups denoted by $R^1$ are exemplified by methyl, ethyl, isopropyl, n-butyl, octyl, and phenyl; the alkoxy groups are exemplified by methoxy, ethoxy, propoxy, and butoxy; the thioalkoxy groups denoted by $R^1$ are exemplified by a thioalkoxy group formed by substituting a sulfur atom for the oxygen atom of the above-mentioned alkoxy group; the dialkylamino groups denoted by $R^1$ are exemplified by $C_{1-10}$ diorganoamino groups, such as, dimethylamino, diethylamino, diisopropylamino, di-n-butylamino, and diphenylamino; the unsubstituted organosilyl groups denoted by $R^2$ are exemplified by trimethylsilyl, phenyldimethylsilyl, and vinyldimethylsilyl; and the organosiloxy-substituted organosilyl groups denoted by $R^2$ are exemplified by trimethylsiloxydimethylsilyl.

Illustrative of the benzophenone derivatives represented by Formula I above are 4-methyl-4'-trimethylsilyl benzophenone, 4-ethyl-4'-trimethylsilyl benzophenone, 4-isopropyl-4'-trimethylsilyl benzophenone, 4-n-butyl-4'-trimethylsilyl benzophenone, 4-chloro-4'-trimethylsilyl benzophenone, 4-bromo-4'-trimethylsilyl benzophenone, 4-methoxy-4'-trimethylsilyl benzophenone, 4-ethoxy-4'-trimethylsilyl benzophenone, 4-isopropoxy-4'-trimethylsilyl benzophenone, 4-n-butoxy-4'-trimethylsilyl benzophenone, 4-thiomethoxy-4'-trimethylsilyl benzophenone, 4-dimethylamino-4'-trimethylsilyl benzophenone, 4-diethylamino-4'-trimethylsilyl benzophenone, 4-methyl-4'-phenyldimethylsilyl benzophenone, 4-ethyl-4'-phenyldimethylsilyl benzophenone, 4-chloro-4'-phenyldimethylsilyl benzophenone, 4-bromo-4'-phenyldimethylsilyl benzophenone, 4-methoxy-4'-phenyldimethylsilyl benzophenone, 4-ethoxy-4'-phenyldimethylsilyl benzophenone, 4-thiomethoxy-4'-phenyldimethylsilyl benzophenone, 4-dimethylamino-4'-phenyldimethylsilyl benzophenone, 4-diethylamino-4'-phenyldimethylsilyl benzophenone, 4-methyl-4'-trimethylsiloxydimethylsilyl benzophenone, 4-chloro-4'-trimethylsiloxydimethylsilyl benzophenone, 4-methoxy-4'-trimethylsiloxydimethylsilyl benzophenone, 4-triomethoxy-4'-trimethylsiloxydimethylsilyl benzophenone, 4-dimethylamino-4'-trimethylsiloxydimethylsilyl benzophenone, 4-thiomethoxy-4'-trimethylsiloxydimethylsilyl benzophenone, 4-dimethylamino-4'-trimethylsiloxydimethylsilyl benzophenenone, 4-vinyldimethylsilyl benzopheneone, 4-methyl-4'-vinyldimethylsilyl benzophenone, 4-methoxy-4'-vinyldimethylsilyl benzophenone, 4-ethoxy-4'-vinyldimethylsilyl benzophenone, 4-thiomethoxy-4'-vinyldimethylsilyl benzophenone, 4-chloro-4'-vinyldimethylsilyl benzophenone, 4-dimethylamino-4'-vinyldimethylsilyl benzophenone, 4-diethylamino-4'-vinyldimethylsilyl benzophenone, 3-methyl-4'-trimethylsilyl benzophenone, 3-ethyl-4'-trimethylsilyl benzophenone, 3-methoxy-4'-trimethylsilyl benzophenone, 3-thiomethoxy-4'-trimethylsilyl benzophenone, 3-dimethylamino-4'-trimethylsilyl benzophenone, 3-methyl-4'-phenyldimethylsilyl benzophenone, 3-ethyl-4'-phenyldimethylsilyl benzophenone, 3-methoxy-4'-phenyldimethylsilyl benzophenone, 3-thiomethoxy-4'-phenyldimethylsilyl benzophenone, 3-dimethylamino-4'-phenyldimethylsilyl benzophenone, 3-methyl-4'-trimethylsiloxydimethylsilyl benzophenone, 3-methoxy-4'-trimethylsiloxydimethylsilyl benzophenone, 3-thiomethyoxy-4'-trimethylsiloxydimethylsilyl benzophenone, 3-dimethylamino-4'-trimethylsiloxydimethylsilyl benzophenone, 2-methyl-4'-trimethylsilyl benzophenone, 2-methoxy-4'-trimethylsilyl benzophenone, 2-methoxy-4'-trimethylsilyl benzophenone, 2-thiomethoxy-4'-trimethylsilyl benzophenone, 2-dimethylamino-4'-trimethylsilyl benzophenone, 2-methyl-4'-phenyldimethysilyl benzophenone, 2-thiomethoxy-4'-phenyldimethysilyl benzophenone, 2-methoxy-4'-phenyldimethylsilyl benzophenone, 2-dimethylamino-4'-phenyldimethylsilyl benzophenone, 2-methyl-4'-trimethylsiloxydimethylsilyl benzophenone, 2-methoxy-4'-trimethylsiloxydimethylsilyl benzophenone, 2-thiomethoxy-4'-trimethylsiloxydimethylsilyl benzophenone, 2-dimethylamino-4'-trimethylsiloxydimethylsilyl benzophenone, 4-methyl-3'-trimethylsilyl benzophenone, 4-methoxy-3'-trimethylsilyl benzophenone, 4-dimethylamino-3'-trimethylsilyl benzophenone, 4-methyl-3'-trimethylsiloxydimethylsilyl benzophenone, 4-methoxy-3'-trimethylsiloxydimethylsilyl benzophenone, 4-dimethylamino-3'-trimethylsiloxydimethylsilyl benzophenone, 4-methyl-3',5'-bis(trimethylsilyl) benzophenone, 4-methoxy-3',5'-bis(trimethylsilyl) benzophenone and 4-dimethylamino-3',5'-bis(trimethylsilyl) benzophenone.

The benzophenone derivatives of the present invention can be synthesized by several convenient methods. One example of the methods involves reacting a benzaldehyde derivative of the general formula

where $R^1$ is as defined above and $m$ is an integer of from 1 to 5, with a Grignard reagent prepared from an organosilyl-substituted halobenzen of the general formula

where $R^2$ is as defined above, X is a halogen atom, and $n$ is an integer of from 1 to 5, and oxidizing the reaction product, i.e., a diarylcarbinol derivative, to the corresponding benzophenone derivative.

A further example involves reacting a Grignard reagent prepared from a substituted halobenzene of the general formula

where $R^1$, X and $m$ are as defined above, with an organosilyl-substituted benzaldehyde of the general formula

where $R^2$ and $n$ are as defined above, and oxidizing the reaction product, i.e., a diarylcarbinol derivative to the corresponding benzophenone derivative.

The oxidation of the diarylcarbinol derivatives in the preparation of the benzophenone derivatives useful in the photosensitizers of this invention can be carried out by various known methods. From commercial points of view, the following two methods are preferred and advantageous.

1. The diarylcarbinol derivative as the product of the above-mentioned Grignard reaction is oxidized with an aldehyde of the general formula $$R^3CHO \qquad (VI)$$

where $R^3$ is a monovalent $C_{1-9}$ hydrocarbon group, or a ketone of the general formula $$R^4COR^5 \qquad (VII)$$

where $R^4$ and $R^5$ are the same as $R^3$ above. This oxidation reaction is known by the name of the Oppenauer oxidation reaction.

2. The diarylcarbinol isolated from the magnesium salt is oxidized by an oxidizing agent of the chromic anhydride-pyridine mixture (Cornforth reagent) or of chromic anhydride-surfuric acid mixture (Jones reagent).

The Grignard reagents used in the above-described Grignard reaction can be readily obtained by use of dialkyl ethers, such as, diethyl ether or alicyclic ethers, such as, tetrahydrofuran as the solvent.

In carrying out the Grignard reaction, it is advisable to use the benzaldehyde derivative of Formula II or the benzaldehyde derivative of Formula V containing an organic silicon unit as dissolved in any one of the above-specified solvents, optionally diluted with a hydrocarbon solvent. Temperatures, periods of time and other conditions under which the Grignard reaction is conducted are variable depending on the kinds of substituents, though a satisfactory reaction can, in general, be completed with heating and stirring under reflux over a period of 1 to 5 hours.

The aldehydes and ketones used as the oxidizing agents in the above-mentioned Oppenauer oxidation are exemplified by acetaldehyde, propionaldehyde, benzaldehyde, acetone and cyclohexanone.

In the process of synthesizing the benzophenone derivatives useful as the photosensitizers, it is most usual and easiest to introduce the above-mentioned substituents $R^1$ and $R^2$ so that each of them is connected to the benzene ring concerned in the para position with respect to the carbonyl group. They may, however, be connected in either the meta or ortho position, to produce similarly useful benzophenone derivatives. The number of each substituent to be connected to one benzene ring as indicated by m or n in Formula I is from 1 to 5, preferably 1 or 2 from the synthetical point of view. When it exceeds 2 on one benzene ring, the substituents concerned may not necessarily be of the same kind the different kinds.

The photosensitizers comprising at least one benzophenone derivative of this invention as their main components can be incorporated into various photopolymerizable resins to form photocurable compositions. Suitable photopolymerizable resins for the purpose include (a) photopolymerizable silicone resins (see Japanese Public Disclosure Nos. 48-16991 and 48-19682), (b) resins have a photosensitive cinnamoyl group, (c) resins formed from a monomer having a photosensitive acryloxy group, and (d) other photopolymerizable resins. These resins will be illustrated in the following.

a. The photopolymerizable silicone resin is an organopolysiloxane containing at least one photopolymerizable organic silicon unit of the general formula:

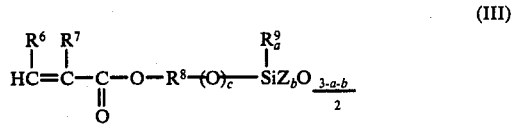

(III)

where $R^6$ is a hydrogen atom or an unsubstituted or halogen-substituted phenyl group, $R^7$ is a hydrogen atom or a methyl group, $R^8$ is an unsubstituted or halogen-substituted divalent $c_{1-10}$ hydrocarbon group, $R^9$ is an unsubstituted or halogen-substituted monovalent $C_{1-10}$ hydrocarbon group, $Z$ is a hydroxy or $C_{1-4}$ alkoxy group, and $a$ is 0,1 or 2, $b$ is 0,1 or 2, with the proviso that $(a+b)=0,1$, or 2, and $c$ is 0 or 1.

The photopolymerizability of the above-mentioned organopolysiloxane is due to the presence of the organic group of the general formula:

(IX)

where $R^6$ and $R^7$ are as defined above. This organic group is exemplified by acryloxy, methacryloxy, cinnamoyloxy, and halogenocinnamoyloxy groups.

The unsubstituted or halogen-substituted divalent $C_{1-10}$ hydrocarbon group denoted by $R^8$ in formula VIII is exemplified by alkylene groups, such as, methylene, propylene, butylene, and 2,2-dimethyl-1,3-propylene; arylene groups, such as, phenylene; alkarylene groups, such as, phenethylene; and their halogen-substituted analogues. The unsubstituted or halogen-substituted monovalent $C_{1-10}$ hydrocarbon group denoted by $R^9$ is exemplified by alkenyl groups, such as, vinyl and allyl; cycloalkenyl groups, such as, cyclohexenyl; alkyl groups, such as, methyl, ethyl, propyl and octyl; aryl groups, such as, phenyl; aralkyl groups, such as benzyl and phenethyl; and alkaryl groups, such as, xylyl and tolyl, and their halogen-substituted analogues, such as, chloromethyl, trichloroethyl, perfluorovinyl, trifluoropropyl and chlorotolyl groups.

Further, the organopolysiloxane containing at least one photopolymerizable organic silicon unit of Formula VIII as described above may be such an organic silicon compound that additionally contains a unit of the general formula

(X)

where $R^{10}$ is the same as $R^9$ above, $Z$ is as defined above, and each of $d$ and $e$ is 0, 1, 2 or 3, with the proviso that $(d+e) = 0, 1, 2$ or 3, the unit being bonded to the unit of Formula VIII by the siloxane linkage ($\equiv$Si—O—Si$\equiv$). Organic silicon compounds comprising one or more units of Formulas VIII and X may be oily, rubbery or resinous in appearance, and straight-chained, branch-chained, or cyclic in molecular configuration.

b. The resins having a cinnamoyl group or cinnamylidene group ($C_6H_5$—CH=CHCO—) as the photosensitive radical are, for example, polyvinyl cinnamate, polyvinyl cinnamylidene acetate, polyvinyl benzoate cinnamylidene acetate, polyvinylcarbuethoxymethylcarbamate cinnamylidene acetate, polyvinyl acetate cinnamylidene acetate, coumarin resin, and polyvinyl benzal acetophenone.

c. The resins comprising a monomer having an acryloxy group as the photosensitive radical and working as photopolymerizable component and crosslinking agent are exemplified by polymers of acrylic compounds, such as, methylacrylate, methylmethacrylate, triethyleneglycol diacrylate, pentaerythritol triacrylate, and glycerol diacrylate and acrylamide compounds, such as, acrylamide, N,N'-methylene-bisacrylamide, 3-xylene bisacrylamide, or cellulose esters and polyvinyl alcohol modified with the acrylate or acrylamide compounds as named above.

d. Other photopolymerizable resins include photosensitive unsaturated polyester resins that may be produced from a polybasic acid, such as, fumaric acid and a polyhydric alcohol, such as, polyethylene glycol.

The photosensitizers of the present invention are especially suitable for use in combination with the photopolymerizable organosilicon resins, among the photopolymerizable resin groups (a) to (d) above.

To explain about the photocurable compositions formulated by incorporation of a benzophenone derivative, they comprise at least one photopolymerizable organopolysiloxane expressed by the above-mentioned Formula VIII and a photosensitizer comprising a benzophenone derivative expressed by the above-mentioned Formula I as its main components.

The photocurable compositions may also comprise a solvent or diluent, if necessary, for example, to control their viscosity at a level suitable for coating the substrate surfaces. Such solvents are exemplified by ketones, such as, methylethyl ketone and methylisobutyl ketone, aromatic hydrocarbons, such as, benzene, toluene, and xylene, and chlorinated hydrocarbons, such as, trichloroethylene and tetracchloroethylene. The diluents useful for the purpose include, for example, alcohols and esters that are inert to the organopolysiloxane having at least one photopolymerizable organic silicon unit of Formula VIII.

Moreover, the compositions may comprise any of the thermal polymerization inhibitors, including quinone derivatives, such as, hydroquinone and benzoquinone, amines, hydrazine salts, aldehydes, and ascorbic acid, and fillers used in connection with known photopolymerizable compositions. Any appropriate amount of these additives may be used, but, since thermal polymerization inhibitors are intended to improve the stability during storage (prevention of reaction in the dark) of the compositions and prevent thermal polymerization, when the solvent has evaporated from the compositions after they have been applied over substrata, it is preferred to use the polymerization inhibitor in an amount in the range of about 0.01% to 1% by weight, based on the weight of the organopolysiloxane having at least one photopolymerizable organic silicon unit of Formula VIII.

The benzophenone derivatives of this invention as photosensitizers are capable of giving a remarkably advanced photosensitivity to photopolymerizable organopolysiloxanes, and very compatible or miscible with the photopolymerizable organopolysiloxanes in an amount up to 20% or more by weight of the organopolysiloxane. In contrast thereto, conventional photosensitizers exemplified by Michler's ketone can be dissolved in an amount of only 2% or less by weight of the organopolysiloxane. In other words, the photocurable compositions can have a higher concentration and, accordingly, a superior photosensitivity can be obtained with the photosensitizers of this invention than with the conventional photosensitizers. Moreover, the photocurable compositions according to the invention can easily be controlled with respect to their photosensitivity in a more precise manner and within a wider range than those comprising the conventional Michler's keytone-type photosensitizers. Furthermore, due to an excellent compatibility of the photosensitizers of the invention with the photopolymerizable organopolysiloxanes, the compositions made therefrom can be stored for a long period of time without the occurrence of separation and crystallization of the photosensitizers in the compositions.

The photocurable compositions in accordance with this invention, when applied over substrata and dried and exposed to ultraviolet light or strong visible light, give extremely strong and insoluble films, having superior heat-, chemical-, and corrosion resistance as well as outstanding repellency against oils. Any part of the compositions that is not exposed to light can be easily washed away with a solvent, so that any pattern can be formed without difficulty. The exact mechanism by which the exposed part forms a cured film is not known, but, presumably, when the photocurable compositions applied over substrata and dried are exposed to light, the photopolymerizable organic groups of the formula IX contained in the organopolysiloxane having the unit of the formula VIII become excited by the light and polymerization takes place thereby forming a hard and insoluble film. The velocity of the polymerization is greatly increased in the presence of a photosensitizer by the energy transfer from the latter which has absorbed the energy of light effectively. On the other hand, the photopolymerizable organosilicon resin present on the areas not exposed to light remains unchanged and is therefore easily washed away with a solvent. The films thus formed and cured by the light may be subject to further curing with heat to increase their hardness to its maximum.

Substrata which are coated by the photocurable composition of the invention are plates of metals, such as, copper, aluminum, and stainless steel; glass plates; and synthetic plastics plates. The coating can be conducted by known methods, e.g., by flow, dip, whirler, spinner, spray or roller coating. The light source to which the photocurable composition is exposed is a lamp giving off a light rich in ultraviolet light which is, such as, a xenon lamp, or a low-pressure or high-pressure mercury lamp.

To produce a cured film on a substratum with the photocurable composition, a thin layer of the composition is applied over the substratum and a positive pattern is placed closely thereon, followed by exposure to light under reduced pressure thereby to avoid any adverse influence to be caused by the existence of oxygen and to ensure the close contact between the substratum and the pattern. Thereafter, the layer of photocurable composition is developed by washing with a solvent, dried and further cured to completion with heat; a pattern of the film is formed in the part of the composition exposed to the light. Films thus obtained have superior heat-, solvent-, and corrosion-resistance as well as oil-repellency and can therefore be very advantageously put to various use such as plate-making in printing, or resists for etching in printed circuit making. Furthermore, the films have very strong resistance against spattering, and therefore can be used as resists for ion-etching.

Now, a dry-planographic printing plate comprising a base having non-image areas constituted of a polymerized and cured layer of a photocurable composition containing the photopolymerizable organosilicon resin and the benzophenone derivative in accordance with this invention will be explained hereinafter.

Referring for the purpose to the drawings which consist of a series of four FIG. 1, 2, 3, and 4, the manufacture of the dry-planographic printing plates is illustrated as follows.

Figure 2:
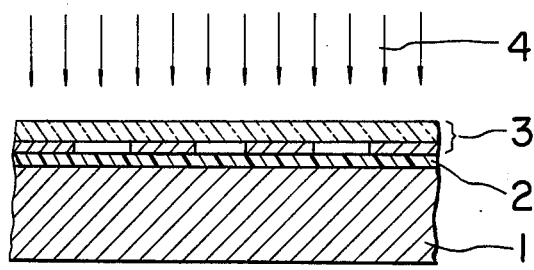
FIG. 2 represents a sectional view depicting the exposure to light of the dry-planographic plate comprising the base, layer of the photopolymerizable composition, and overlying positive pattern.
Figure 3:
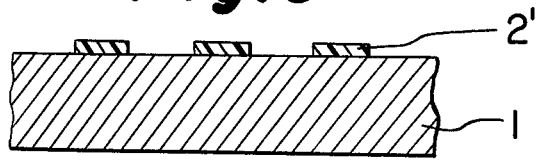
FIG. 3 represents a sectional view illustrating an exposed and developed plate of the present invention.

As shown in FIG. 1, the photocurable composition (diluted with a solvent, if necessary) is applied over base 1 and dried to make a layer 2, about 3 to 10 μm thick. Overlying layer 2 is a pattern 3, through which the composite is exposed to ultraviolet light or strong visible light 4, as shown in FIG. 2 followed by development and fixing. FIG. 3 shows the light-exposed portions of layer 2, i.e., polymerized and cured layer 2', having superior properties of heat-, solvent-, and chemical resistances as well as oil-repellency, whereas the unexposed portions have been washed away as the result of the development procedure.

As the base plate 1 a metal plate, such as, copper, aluminum, stainless steel, zinc, or iron plate may be used. It is preferred to clean its surface by any suitable means before it is coated with the photocurable composition. It is also preferred to apply a primer to the surface of base plate 1 by any of the known methods, using rollers, brushes, or rods or by spraying. Usable primers include, for example, silanes, such as, vinyl-tris(2-methoxyethoxy) silane, 3-glycidoxypropyltrimethoxysilane, 3-methacryloxypropyltrimethoxysilane, N-(3-trimethoxysilylpropyl) ethylene diamine, and 3-aminopropyltriethoxysilane, either alone or in mixture, and partially hydrolyzed or cohydrolyzed products thereof.

As the positive pattern 3 is used, for example, a silver emulsion positive transparency.

In the making of the dry-planographic printing plates in accordance with this invention, the photocurable composition, prior to application to substrata, may be diluted by solvents including the above-mentioned ketone solvents, aromatic hydrocarbons, halogenated hydrocarbons, alcohols, and esters.

The photocurable compositions according to the invention may also comprise thermal polymerization inhibitors and fillers, such as, finely divided silica.

To produce a positive picture with the photocurable composition on the dry-planographic printing plate according to a preferred embodiment of this invention, the base 1 is coated with the photocurable composition in a thin layer 2', a positive pattern 3 is closely placed thereon, and the composite is exposed to light under reduced pressure. Then the layer of photocurable composition is developed, dried, and further cured to completion with heat, to give a photopolymerized and cured layer 2' as the non-image area, having superior heat-, solvent-, and corrosion-resistance as well as oil-repellency in the part of the composition exposed to light, as shown in FIG. 3.

Developing solvents useful in the development of the layer of photocurable composition are exemplified by solvents, such as, aliphatic and aromatic hydrocarbons, chlorinated hydrocarbons, and ketones, e.g., toluene, xylene, cyclohexane, methylethyl ketone, methylisobutyl ketone, and trichloroethylene.

Figure 4:
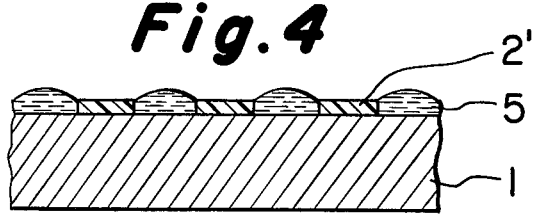
FIG. 4 represents a sectional view showing the printing ink adhering to the base surface.

When the dry-planographic printing plate in accordance with this invention is used for press printing and , specifically, the printing ink is supplied by ink rollers over the printing plate, the ink is not transferred to the surface of the layer of photocurable composition 2' as the non-image area, but to the bare or naked surface of the base 1, to form the ink layer 5 as shown in FIG. 4. This is because cohesion between the printing ink and layer 2' is low compared to the cohesion between the ink and the roller surface or between the particles of the ink themselves. By using the above method, the dampening solution hitherto required in the planographic printing can be dispensed with.

Further, according to the method of this invention, the dry-planographic printing plates in accordance with this invention can ensure an excellent printability as well as the clearness of prints due to the great differences in the physical properties existent between the cured layer of photocurable composition as the non-image areas and the bare metal surface as the image areas.

In the following, the references are to illustrate the procedures for the preparation of the photopolymerizable organosilicon resins suitable to make the photocurable compositions with the benzophenone derivatives of the invention as the photosensitizer. In the references and examples to follow, parts and percentages are all based on weight and the viscosities are all at 25° C.

Reference 1

247 parts of a 15% solution of α, ω-dihydroxydimethylpolysiloxane expressed by the formula

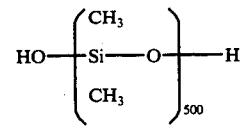

in toluene and 60 parts of a 30% solution of the hydrolyzate of phenyltrichlorosilane in toluene were mixed together, and to the mixture were added 0.25 part of 3-methacryloxypropyltrimethoxysilane, 0.01 part of dibutylhydoxytoluene and 0.1 part of dibutyltindilaurate. The resulting mixture was subjected to a further condensation reaction under reflux of toluene for 48 hours, while removing the water produced, to obtain a solution of a siloxane copolymer, having a viscosity of 28.4 cS and a solid content of 30%.

Reference 2.

To 1,022 parts of toluene were added 258 parts of dimethyldichlorosilane and 53 parts of phenyltrichlorosilane, and the resulting mixture was hydrolyzed by being dropped into 1,124 parts of water, followed by washing with water, neutralization and a dehydration treatment, to produce a solution of cohydrolyzate having a 15% concentration of siloxane. To 1,200 parts of the cohydrolyzate solution thus produced were added 7.4 parts of 3-methacryloxypropylmethyldimethoxysilane, 0.1 part of methoxyhydroquinone and 0.4 part of tin dioctoate. The resulting mixture was then subjected to a condensation reaction under reflux of toluene for 5 hours while removing water produced, to obtain a solution of a siloxane copolymer, having a viscosity of 20.1 cS and a solid content of 15%.

Reference 3.

To 194 parts of a 20% solution of the hydrolyzate of phenyltrichlorosilane in toluene were added dropwise 2.36 parts of pyridine as the hydrogen chloride acceptor and 743 parts of a 20% solution of a siloxane expressed by the formula

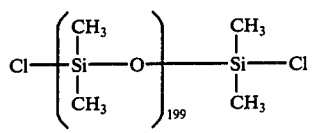

in toluene, over a period of 1 hour. The reaction product was freed, by washing with water, from the hydrochloride of pyridine produced and any remaining unreacted pyridine, and then dehydrated, to obtain a solution of siloxane of 15% concentration. To this solution were added, in turn, 4.96 parts of 3-methacryloxypropyltrimethoxysilane, 0.5 part of paratoluene-sulfonic acid as the condensation catalyst and 0.1 part of dibutylhydroxytoluene. The mixture was subjected to a condensation reaction under reflux of toluene for 35 hours, to obtain a solution of a siloxane copolymer having a viscosity of 10.6 cS and a solid content of 20%.

Reference 4.

To 64.5 parts of a 10% solution of the hydrolyzate of phenyltrichlorosilane in toluene were added dropwise 0.23 part of pyridine and 297 parts of a 10% solution of a siloxane expressed by the formula

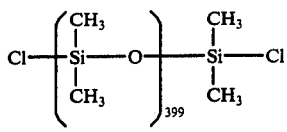

in toluene, over a period of 1 hour at room temperature. The resulting reaction was freed, by washing with water, from the hydrochloride of pyridine produced and any unreacted pyridine remaining, and then dehydrated, to obtain a solution of siloxane of 10% concentration. To this solution were added 0.5 part of 3-methacryloxytriethoxysilane and 0.1 part of tin dioctoate, for reaction under reflux of toluene for 5 hours, to obtain a solution of a siloxane copolymer having a viscosity of 18.9 cS and a solid content of 10%.

Reference 5.

To 430 parts of a 15% solution of the hydrolyzate of phenyltrichlorosilane in toluene, were added dropwise 2.3 parts of pyridine and 2,470 parts of a 15% solution of α,ω-dichlorodimethylpolysiloxane expressed by the formula

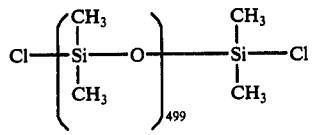

in toluene, at room temperature. The reaction product was freed, by washing with water, from the hydrochloride of pyridine produced and pyridine remaining unreacted, to obtain a solution of a copolymer. To the solution thus obtained were added, in turn, 62 parts of 3-methacryloxypropyltrimethoxysilane, 0.5 part of hydroquinone and 0.5 part of dibutyltin dilaurate, for a condensation reaction under reflux of toluene for 5 hours, to finally obtain a solution of a siloxane copolymer having a viscosity of 31.0 cS and a solid content of 15%.

Reference 6.

To 86 parts of a 15% solution of the hydrolyzate of phenyltrichlorosilane in toluene was added 0.23 part of pyridine as the hydrogen chloride acceptor. The mixture having been well stirred was subjected to a condensation reaction at room temperature for 1 hour by adding thereto dropwise, 247 parts of a 15% solution of a polysiloxane expressed by the formula

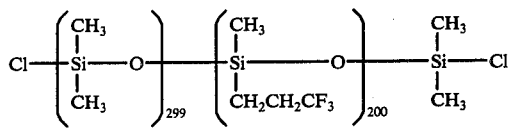

in toluene, followed by washing treatment to remove the hydrochloride of pyridine and any unreacted pyridine remaining, to obtain a 15% solution of a siloxane. To this solution were added 0.5 part of 3-methacryloxypropyltrimethoxysilane and 0.1 part of dibutyltin dilaurate, and the solution mixture was then reacted so that the condensation took place under reflux of toluene for 8 hours while removing the water produced, to finally obtain a solution of a siloxane copolymer, having a viscosity of 35.0 cS and a solid content of 15%.

Reference 7.

374 parts of 3-methacryloxypropoxytributoxysilane, 592 parts of octamethylcyclotetrasiloxane, 729 parts of octaphenylcyclotetrasiloxane, and 2.0 parts of anhydrous ferric chloride were put into a three-necked flask, and the resulting mixture was stirred while being heated and then kept at 130 ° C for 13 hours. Subsequently, the mixture was cooled, and the ferric chloride was filtered off by use of active charcoal as an absorbent, to obtain 1,705 parts of a colorless, transparent, liquid photopolymerizable silicon compound in a 96% yield, which silicon compound proved to have a viscosity of 250 cS.

Reference 8.

573 parts of α,ω-dichlorodimethylpolysiloxane, having an average molecular weight of 573 and expressed by the formula

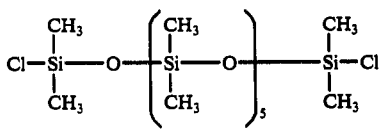

were added dropwise over 1 hour to a mixture of 144 parts of acrylic acid, 300 parts of toluene, and 176 parts of pyridine while being stirred in a three-necked flask. The mixture was further stirred at 60° C for 3 hours. When the reaction ceased, the reaction mixture was cooled, and pyridine hydrochloride was removed by filtration and toluene by distillation under reduced pressure, to obtain 620 parts of a colorless, transparent, liquid photopolymerizable silicon compound in a 96% yield, having a viscosity of 18 cS.

Reference 9.

Into a four-necked flask, were put 152 parts of straight-chained α,ω-dihydroxydimethylpolysiloxane, having a molecular weight of 758 and expressed by the formula:

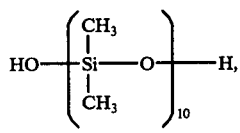

496 parts of 3-methacryloxypropyl trimethoxysilane, and 0.2 part of potassium acetate, and the mixture was stirred at 80° C under an atmosphere of nitrogen, the methanol generated was removed through a condenser equipped to the flask. When the distillation of methanol ceased, the reaction product was cooled and potassium acetate was filtered off, giving a pale yellow and transparent photopolymerizable silicon compound. The siloxane (188 parts), was obtained in a 96% yield, and had a viscosity of 13 cS.

Reference 10.

In a four-necked flask were placed 175 parts of straight-chained α,ω-dihydroxymethylphenylpolysiloxane, having an average molecular weight of 1,746, and expressed by the formula:

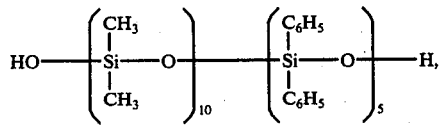

36 parts of 3-cinnamoyloxypropyltriacetoxysilane and 175 parts of toluene, and the mixture was heated to 75–80° C. After the mixture was stirred for 30 minutes, 5.4 parts of water were added to it, and the mixture was further stirred for 4 hours. When the reaction was over, the reaction product was distilled under reduced pressure, and toluene and acetic acid generated were distilled off, giving a pale yellow and transparent photopolymerizable silicon compound (188 parts) in 95% yield. The viscosity of the siloxane thus prepared proved to be 153 cS.

Reference 11.

578 parts of αω-dimethoxydimethylpolysiloxane, having an average molecular weight of 1,156, and expressed by the formula

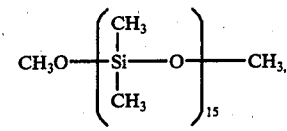

578 parts of toluene, 165 parts of cinnamic acid, and 1.0 part of p-toluenesulfonic acid were put into a three-necked flask, equipped with a distilling column. The mixture was then stirred while being kept at 115 °C. The generated methanol was removed by fractional distillation by means of the distilling column. When no more generation of methanol was observed, the temperature was lowered, and with 35 parts of sodium carbonate added to the reaction product, the mixture was heated up to 80 °C for 2 hours, and after the reaction was over, any excess sodium carbonate and the p-toluenesulfonic acid sodium salt formed were removed by filtration, and the, toluene was removed by distillation under reduced pressure, to give 682 parts of pale yellow, transparent, liquid photopolymerizable silicon compound in 95% yield, having a viscosity of 36 cS.

Reference 12.

573 parts of α,ω-dichlorodimethylpolysiloxane, having an average molecular weight of 573 and expressed by the formula

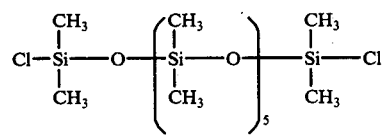

were added dropwise over 1 hour to a mixture of 144 parts of acrylic acid, 300 parts of toluene and 176 parts of pyridine while being stirred in a three-necked flask. The mixture was further stirred at 60 °C for 3 hours. When the reaction ceased, the reaction mixture was cooled, and the pyridine hydrochloride formed was removed by filtration and the toluene by distillation under reduced pressure, to give 620 parts of a colorless, transparent, liquid photopolymerizable silicon compound in a 96% yield, having a viscosity of 180 cS.

Reference 13.

To 64.5 parts of a 10% solution of the hydrolyzate of phenyltrichlorosilane in toluene were added dropwise 0.23 part of pyridine and 297 parts of a 10% solution of a siloxane expressed by the formula

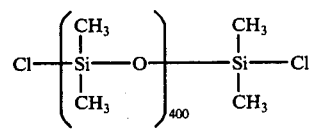

in toluene, over 1 hour at room temperature. The resulting reaction product was freed, from the hydrochloride of produced and any pyridine remaining unreacted pyridine by washing with water, and then dehydrated, to give a solution of siloxane of 10% concentration. To this solution were added 0.5 part of 3-methacryloxytriethoxysilane and 0.1 part of tin dioctoate and the mixture was heated under reflux of toluene for 5 hours, to give a solution of siloxane copolymer having a viscosity of 15.6 cS and a solid content of 10%.

EXAMPLE 1

A Grignard reagent prepared from 0.2 mole of 4-trimethylsilylchlorobenzene and 0.2 mole of magnesium was reacted with 0.2 mole of 4-dimethylaminobenzaldehyde. The resulting reactant was subjected to oxidation by the Oppenauer method, to yield 4-dimethylamino-4'-trimethylsilyl benzophenone.

EXAMPLE 2

4-Dimethylamino-4'-trimethylsilylbenzhydrol prepared from 4-dimethylaminobenzaldehyde and 4-trimethylsilylchlorobenzene was oxidized by a Cornforth reagent, to yield 4dimethylamino-4'-trimethylsilyl benzophenone.

EXAMPLES 3–23

Various benzophenone derivatives were prepared in accordance with the same procedure as in Example 1 excepting that 0.2 mole of a benzaldehyde derivative was used instead of 4-dimethylaminobenzaldehyde and 0.2 mole of a halobenzene derivative was used instead of 4-trimethylsilylchlorobenzene. The particulars are set out as follows.

| Example No. | Benzaldehyde derivative | Halobenzene derivative | Benzophenone derivative |
|---|---|---|---|
| 3 | 4-Methyl-benzaldehyde | 4-Trimethylsilylchlorobenzene | 4-Methyl-4'-trimethylsilylbenzophenone |
| 4 | 3-Methyl-benzaldehyde | " | 3-Methyl-4'-trimethylsilylbenzophenone |
| 5 | 4-Methoxy-benzaldehyde | " | 4-Methoxy-4'-trimethylsilylbenzophenone |
| 6 | 3-Methoxy-benzaldehyde | " | 3-Methoxy-4'-trimethylsilylbenzophenone |
| 7 | 4-Dimethyl-benzaldehyde | 3-Trimethylsilylchlorobenzene | 4-Dimethyl-3'-trimethylsilyl benzophenone |
| 8 | 4-Methyl-benzaldehyde | 4-Trimethylsiloxy-dimethylsilylchlorobenzene | 4-Methyl-4'-trimethylsiloxydimethylsilyl benzophenone |
| 9 | 3-Methyl-benzaldehyde | " | 3-Methyl-4'-trimethylsiloxy-dimethylsilyl-benzophenone |
| 10 | 4-Methoxy-benzaldehyde | " | 4-Methoxy-4'-trimethylsiloxy-dimethylsilyl-benzophenone |
| 11 | 3-Methoxy-benzoldehyde | " | 3-Methoxy-4'-trimethylsiloxy-dimethylsilyl-benzophenone |
| 12 | 4-Dimethyl-amino benzaldehyde | " | 3-Dimethylamino-4'-trimethyl-siloxydimethyl-silyl benzophenone |
| 13 | 4-Dimethyl-amino-benzaldehyde | 3-Trimethyl-siloxy-dimethyl-silyl-chlorobenzene | 4-Dimethylamino-3'-trimethyl-siloxydimethyl-silyl benzophenone |
| 14 | 4-Methoxy-benzaldehyde | 4-Dimethyl-vinylsilyl-chloro-benzene | 4-Methoxy-4'-dimethylvinyl-silyl benzophenone |
| 15 | 3-Methoxy-benzaldehyde | " | 3-Methoxy-4'-dimethylvinyl-silyl benzophenone |
| 16 | 4-Dimethyl-amino-benzaldehyde | " | 4-Dimethylamino 4'-dimethylvinyl-silyl benzophenone |
| 17 | 4-Methoxy-benzaldehyde | 4-Dimethyl-phenylsilyl-chlorobenzene | 4-Methoxy-4'-dimethylphenyl-silyl benzophenone |
| 18 | 3-Methoxy-benzaldehyde | " | 3-Methoxy-4'-dimethylphenyl-silyl benzophenone |
| 19 | 4-Dimethyl-amino-benzaldehyde | " | 4-Dimethylamino-4'-dimethyl-phenylsilyl benzophenone |
| 20 | 4-Methoxy-benzaldehyde | 3,5-bis(tri-methylsilyl)-chlorobenzene | 4-Methoxy-3',5'-bis(trimethyl-silyl) benzophenone |
| 21 | 4-Dimethyl-amino-benzaldehyde | 3,5-bis(tri-methylsilyl)-chlorobenzene | 4-Dimethylamino-3',5'-bis(tri-methylsilyl) benzophenone |
| 22 | 4-Bromo-benzaldehyde | 4-Trimethyl-silylchloro-benzene | 4-Bromo-4'-trimethylsilyl benzophenone |
| 23 | 4-Dimethyl-amino-benzoldehydy | 4-Dimethyl-phenylsilyl-chlorobenzene | 4-Dimethylamino-4'-dimethyl-phenylsilyl benzophenone |

EXAMPLES 24–49

To the photopolymerizable organosilicon resins obtained in accordance with the above-described references 1, 2, and 4–8 was added a certain amount of one benzophenone derivative prepared in accordance with the foregoing examples. The resultant photocurable compositions were measured with respect of their sensitivity (S) to light. The particulars and results are set out as follows.

| Example No. | Photopolymerizable organosilicon resin obtained by: | Benzophenone derivative obtained by: | Amount of benzophenone derivative used, % | Sensitivity (S) |
|---|---|---|---|---|
| 24 | Reference 8 | Example 1 | 10 | 250 |
| 25 | Reference 7 | Example 1 | 10 | 250 |
| 26 | Reference 5 | Example 1 | 1.5 | 43 |
| 27 | Reference 5 | Example 1 | 10 | 693 |
| 28 | Reference 6 | Example 2 | 1.5 | 42 |
| 29 | Reference 6 | Example 2 | 10 | 476 |
| 30 | Reference 4 | Example 3 | 10 | 40 |
| 31 | Reference 4 | Example 4 | 10 | 10 |
| 32 | Reference 4 | Example 5 | 10 | 58 |
| 33 | Reference 4 | Example 6 | 10 | 19 |
| 34 | Reference 2 | Example 7 | 10 | 323 |
| 35 | Reference 1 | Example 8 | 10 | 49 |
| 36 | Reference 1 | Example 9 | 10 | 15 |
| 37 | Reference 1 | Example 10 | 10 | 60 |
| 38 | Reference 1 | Example 11 | 10 | 21 |
| 39 | Reference 1 | Example 12 | 10 | 512 |
| 40 | Reference 1 | Example 13 | 10 | 51 |
| 41 | Reference 1 | Example 14 | 10 | 51 |
| 42 | Reference 1 | Example 15 | 10 | 20 |
| 43 | Reference 1 | Example 16 | 10 | 665 |
| 44 | Reference 6 | Example 17 | 10 | 61 |
| 45 | Reference 6 | Example 18 | 10 | 16 |
| 46 | Reference 6 | Example 19 | 10 | 562 |
| 47 | Reference 5 | Example 20 | 10 | 48 |
| 48 | Reference 5 | Example 21 | 10 | 335 |
| 49 | Reference 7 | Example 22 | 10 | 14 |

For purposes of comparison, a photocurable composition was prepared by adding 1.5% Michler's ketone to the photopolymerizable silicon resin obtained in accordance with Reference 1. The sensitivity of the photocurable composition was found to be as high as 86, whereas the sensitivity of the photopolymerizable silicon resin was only 0.8. However, it was further found in this connection that more than 1.5% Michler's ketone can hardly be compatible wih the photopolymerizable silicon resin and that Michler's ketone tended to be separated out and crystalized on the surface of the resin while stored at room temperature, the sensitivity beginning to lower in about 2 weeks till it becomes about half. On the other hand, the benzophenone derivatives of this the present invention are very compatible with the photopolymerizable resins and capable of maintaining a stable sensitivity over a period of more than 6 months at room temperature.

In the above examples 24–49 and also in Example 50–52 to follow, the sensitivity (S) to light of each photocurable composition was determined by the following manner. To a 15% solution of the photopolymerizable resin in toluene was added the specific amount of the benzophenone derivative, to give the photocurable composition. This photocurable composition was applied over an aluminum plate and then dried at 70° C. Onto the thus treated aluminum plate ultraviolet light having a uniform intensity was applied through the Kodak Grey Scale over a predetermined period of time. As a result, part of the photocurable coating exposed to the light through the Kodak Grey Scale became cured, while the other part where the light had not been allowed to reach remained uncured and was washed away with toluene. Based on the dose of light reaching the boundary between the cured and uncured parts, the sensitivity (S) was computed by the equation $S = (k \cdot \text{antilog } D)/I \cdot t$, $k$ being an arbitrary constant, $D$ being the optical density of the Kodak Grey Scale, $I$ being the intensity of the light, and $t$ being exposure time.

EXAMPLE 50

To a mixture consisting of 100 parts of an aqueous solution of polyvinyl alcohol (44 g/l) having a polymerization degree of 1,400, 100 parts of an aqueous solution of sodium hydroxide (5 mole/l), and 100 parts of methylethylketone was added a solution of cynnamoyl chloride in methylethylketone (1 mole/l), and the mixture was allowed to react under agitation. The reacted solution, from which the organic layer had been removed, was centrifugal, and to the resulting solution petroleum ether was added, to produce a precipitated polyvinylcynnamic acid. The polyvinylcynnamic acid thus obtained as a photopolymerizable resin was mixed with 10% of the 4-dimethylamino-4'-trimethylsilyl benzophenone prepared in accordance of Example 1. the resultant photocurable composition was subjected to the sensitivity test, to determine its sensitivity (S) of 15.

EXAMPLE 51

To a mixture consisting of 40 parts of triethyleneglycoldiacrylate, 60 parts of a methacrylic acid-4-vinylbenzoic acid copolymer, and 1,000 parts of methylethylketone was added 10% of the 4-dimethylamino-4-trimethylsilyl benzophenone prepared in accordance with Example 1. The sensitivity (S) of the resultant photocurable composition was 11.

EXAMPLE 52

To a mixture consisting of 100 parts of the unsaturated polyester resin prepared by synthesizing 50% of polyethyleneglycol (molecular weight: 500), 25% of adipic acid, and 25% of fumaric acid, 20 parts of acrylic acid, and 30 parts of acrylamide was added 10% of the 4-dimethylamino-4-trimethylsilyl benzophenone. The sensitivity (S) of the resultant photocurable composition was 16.

EXAMPLE 53

The benzophenone derivatives and the photopolymerizable organopolysiloxane copolymers obtained in accordance with Examples 1–23 and References 1–13, respectively were mixed under good agitation together with or without toluene in proportions as indicated below.

(a) Benzophenone derivative of Example 3 (4-methyl-4'-trimethylsilyl benzophenone) — 5 parts
Photopolymerizable organopolysiloxane of Reference 10 — 100 parts
Toluene — 1000 parts (b) Benzophenone derivative of Example 10 (4-methoxy-4'-trimethylsiloxydimethylsilyl benzophenone) — 5 parts
Photopolymerizable organopolysiloxane of Reference 11 — 100 parts
Toluene — 1000 parts (c) Benzophenone derivative of Example 5 (4-methoxy-4'-trimethylsilyl benzophenone) — 5 parts
Photopolymerizable organopolysiloxane of Reference 12 — 100 parts
Toluene — 1000 parts (d) Benzophenone derivative of Example 2 (4-dimethylamino-4'-trimethylsilyl benzophenone) — 4.5 parts
Photopolymerizable organopolysiloxane of Reference 2 — 1000 parts (e) Benzophenone derivative of Example 13 (4-dimethylamino-4'-trimethylsiloxydimethylsilyl benzophenone) — 4 parts
Photopolymerizable organopolysiloxane of Reference 13 — 1000 parts (f) Benzophenone derivative of Example 23 (4-dimethylamino-4'-dimethylphenylsilyl benzophenone) — 3 parts
Photopolymerizable organopolysiloxane of Reference 10 — 100 parts
Toluene — 1000 parts (g) Benzophenone derivative of Example 16 (4-dimethylamino-4'-dimethylvinylsilyl benzophenone) — 2 parts
Photopolymerizable organopolysiloxane of Reference 2 — 1000 parts (h) Benzophenone derivative of Example 21 [4-dimethylamino-3',5'-bis-(trimethylsilyl)benzophenone] — 5 parts
Photopolymerizable organopolysiloxane of Reference 13 — 1000 parts Each of the resulting mixtures was applied to an aluminum plate by means of a spinner, to form a coating about 10 μm thick. The coating was then exposed to ultraviolet light projected from an 800 W superhigh-pressure mercury lamp placed 40 cm from the coating over a period of 4 minutes, to produce a strong, cured film having excellent heat-, solvent-, and corrosion-resistance as well as oil repellency.

Further, a storage stability test was carried out on similarly coated aluminum plates by placing and allowing them to stand in an oven heated to 60° C and observing any changes in photosensitivity and any occurrence of thermal fogging. It was found then that even after the lapse of more than 500 hours the films were free of the lowering of their photosensitivity and the occurrence of fogging.

EXAMPLE 54

A mixture was prepared by mixing under sufficient agitation, 5 parts of the 4-dimethylamino-4'-trimethylsilyl benzophenone prepared in Example 1, 100 parts of the photopolymerizable organopolysiloxane of Reference 9, and 1,000 parts of toluene. This mixture was applied to an aluminum plate to form a coating about 10 μm thick. Closely upon the coating thus formed an image transparency was placed under reduced pressure and exposed to light from a 3,000 W xenon lamp 50 cm apart over a period of 2-3 minutes, followed by development, drying, and heat-cure at 150° C, to finally produce a strong, cured film having excellent heat-, solvent-, and corrosion-resistance as well as oil repellency.

The above coating on the aluminum plate was subjected to the same storage stability test as in the preceding example, and found to have equally excellent results.

EXAMPLE 55

4-Methylamino-4'-trimethylsilylbenzhydrol was prepared by a Grignard reagent formulated from 0.2 mole of 4-trimethylsilylchlorobenzene and 0.2 mole of magnesium with 0.2 mole of N-methylaminobenzaldehyde. 0.4 mole of the thus obtained 4-methylamino-4'-trimethylsilylbenzhydrol was dissolved in pyridine, and to the resultant solution was added, dropwise over a period of 40 hours at room temperature, an oxidizing agent prepared by adding 125 ml of pyridine to a solution of 7.5 ml of water and 12.5 mole of chromic anhydride under agitation while being cooled with water. The reaction product was refined by chromatography using silica gel, to obtain 41 g of 4-methylamino-4'-trimethylsilyl benzophenone in a yield of 38%.

To 5 parts of the 4-methylamino-4'-trimethylsilyl benzophenone thus obtained were added 100 parts of the photopolymerizable polysiloxane of Reference 9 and 1,000 parts of toluene under sufficient agitation. The resultant composition was applied over an aluminum plate by means of a spinner to form a coating about 10 μm thick. An image transparency was placed upon the coating under reduced pressure and exposed to light projected from an 800 W superhigh-pressure mercury lamp 40 cm from the coating over a period of 1—2 minutes, followed by washing with methylethylketone, drying, and heat-cure at 150° C, to produce a strong, cured film having excellent heat-, solvent-, and corrosion-resistance, as well as oil repellency.

The above coating on the aluminum plate was subjected to the same storage stability test as in Example 53, and found to have equally excellent results.

EXAMPLE 56

5 parts of the 4-methyl-4'-trimethylsilyl benzophenone of Example 3, 100 parts of the photopolymerizable organosiloxane of Reference 11, and 1,000 parts of toluene were mixed together and well agitated. The mixture was applied to an aluminum plate by a spinner to form a coating about 10 μm thick. An image transparency was placed upon the coating under reduced pressure and exposed to light from an 800 W superhigh-pressure mercury lamp 40 cm apart over a period of 1–2 minutes, followed by washing with methylethylketone, drying, and curing at 150° C, to finally produce a strong, cured film having excellent heat-, solvent-, and corrsion-resistance as well as oil repellency.

The above coating on the aluminum plate was subjected to the same storage stability test as in Example 53, and found to have equally excellent results.

For purposes of comparison, 1,000 parts of the photopolymerizable organopolysiloxane of Reference 13 was mixed with 15 parts or 50 parts of Michler's ketone.

The first mixture, i.e., containing 15 parts of Michler's ketone was applied to an aluminum plate to form a coating about 10 μm thick. The coating was exposed to ultraviolet light from an 800 W superhigh-pressure mercury lamp 40 cm from the coating over a period of 4 minutes, to produce a strong film having excellent heat-, solvent-, and corrosion-resistance. Further to observe the storage stability of the above coating on the aluminum plate, it was placed and allowed to stand in an oven heated to 60° C. It was found that Michler's ketone was separated out on the film surface in 24 hours, inducing the lowering of its photosensitivity.

The second mixture, i.e., containing 50 parts of Michler's ketone was similarly dealt with to form a coating 10 μm thick over an aluminum plate. This coating was then freed of the solvent contained therein and it was observed that Michler's ketone was separated out on the surface of the coating.

EXAMPLE 57

The photocurable composition prepared in accordance with Example 53 (e) was applied to a degreased aluminum plate by the roller coating method, to form a coating about 5 μm thick. This coating was dried at 80° C for 10 minutes, and then a positive pattern was placed thereon and the plate was exposed to light from a 3,000 W xenon lamp over a period of 2–4 minutes, followed by development using a solution consisting of 100 parts of toluene and 150 parts of cyclohexane and then by heat-treatment in an oven kept at 200° C for 20 minutes, to finally obtain a dry-planographic printing plate having non-image areas with cured films of the above-mentioned photocurable composition. The cured films thus formed could be very easily peeled off and had a critical surface tension of 21 dyne/cm. They were repellent to offset printing ink. No dampening solution was required in the prepartion of the above printing plate.

What is claimed is:

1. A benzophenone derivative represented by the general formula

where $R^1$ is selected from the group consisting of a halogen atom, a monovalent $C_{1-10}$ hydrocarbon group, an alkoxy group, a thioalkoxy group, an amino group, and a dialkylamino group, $R^2$ is an unsubstituted or organosiloxy-substituted organosilyl group, and each of $m$ and $n$ is an integer of from 1 to 5.

2. 4-Dimethylamino-4'-trimethylsilyl benzophenone.
3. 4-Methyl-4'-trimethysilyl benzophenone.
4. 3-Methyl-4'-trimethylsilyl benzophenone.
5. 4-Methoxy-4'-trimethylsilyl benzophenone.
6. 3-Methoxy-4'-trimethylsilyl benzophenone.
7. 4-Dimethylamino-3'-trimethylsilyl benzophenone.
8. 4-Methyl-4'-trimethylsiloxydimethylsilyl benzophenone.
9. 3-Methyl-4'-trimethylsiloxydimethylsilyl benzophenone.
10. 4-Methoxy-4'-trimethylsiloxydimethylsilyl benzophenone.
11. 3-Methoxy-4'-trimethylsiloxydimethylsilyl benzophenone.
12. 3-Dimethylamino-4'-trimethylsiloxydimethylsilyl benzophenone.
13. 4-Dimethylamino-3'-trimethylsiloxydimethylsilyl benzophenone.
14. 4-Methoxy-4'-vinyldimethylsilyl benzophenone.
15. 3-Methoxy-4'-vinyldimethylsilyl benzophenone.
16. 4-Dimethylamino-4'-vinyldimethylsilyl benzophenone.
17. 4-Methoxy-4'-phenyldimethylsilyl benzophenone.
18. 3-Methoxy-4'-phenyldimethylsilyl benzophenone.
19. 4-Dimethylamino-4'-phenyldimethylsilyl benzophenone.
20. 4-Methyl-3',5'-bis(trimethylsilyl) benzophenone.
21. 4-Dimethylamino-3',5'-bis(trimethylsilyl) benzophenone.
22. 4-Bromo-4'-trimethylsilyl benzophenone.
23. A process for preparing a benzophenone derivative expressed by the general formula

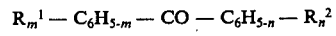

where $R^1$ is selected from the group consisting of a halogen atom, a monovalent $C_{1-10}$ hydrocarbon group, an alkoxy group, a thioalkoxy group, an amino group, and a dialkylamino group, $R^2$ is an unsubstituted or organosiloxy-substituted organosilyl group, and each of $m$ and $n$ is an integer of from 1 to 5, which comprises reacting a Grignard reagent represented by the general formula $$R_m^1 - C_6H_{5-m} - Mg - X$$

where $R^1$ and m are as defined above and X is a halogen atom, with a benzaldehyde derivative represented by the general formula $$R_n^2 - C_6H_{5-n} - CHO$$

where $R^2$ and $n$ are as defined above to form a diarylcarbinol derivative represented by the general formula $$R_m^1 - C_6H_{5-m} - CHOH - C_6H_{5-n} - R_n^2$$

where $R^1$, $R^2$, m and n are as defined above and oxidizing said diarylcarbinol derivative with an oxidizing agent.

24. A process for preparing a benzophenone derivative expressed by the general formula $$R_m^1 - C_6H_{5-m} - CO - C_6H_{5-n} - R_n^2$$

where $R^1$ is selected from the group consisting of a halogen atom, a monovalent $C_{1-10}$ hydrocarbon group, an alkoxy group, a thioalkoxy group, an amino group, and a dialkylamino group, $R^2$ is an unsubstituted or organosiloxy-substituted organosilyl group, and each of $m$ and $n$ is an integer of from 1 to 5, which comprises reacting a Grignard reagent represented by the general formula $$R_n^2 - C_6H_{5-n} - Mg - X$$

where $R^2$ and n are as defined above and X is a halogen atom, with a benzaldehyde derivative represented by the general formula $$R_m^1 - C_6H_{5-m} - CHO$$

where $R^1$ and m are as defined above to form a diarylcarbinol derivative represented by the general formula $$R_n^2 - C_6H_{5-n} - CHOH - C_6H_{5-m} - R_m^1$$

where $R^2$, $R^1$, $n$ and $m$ are as defined above and oxidizing said diarylcarbinol derivative with an oxidizing agent.

25. The process as claimed in claim 23 wherein said oxidizing agent is selected from the group consisting of an aldehyde, a ketone, a mixture of chromic anhydride with pyridine, and a mixture of chromic anhydride with sulfuric acid.

26. The process as claimed in claim 24 wherein said oxidizing agent is selected from the group consisting of an aldehyde, a ketone, a mixture of chromic anhydride with pyridine, and a mixture of chromic anhydride with sulfuric acid.

27. The derivative of claim 1 wherein $R^2$ is an unsubstituted or hydrocarbylsiloxy substituted hydrocarbyl silyl group.

28. The derivative of claim 27 wherein the hydrocarbyl entity is methyl, phenyl and vinyl.

29. The derivative of claim 23 wherein $R^2$ is an unsubstituted or hydrocarbylsiloxy substituted hydrocarbyl silyl group.

30. The derivative of claim 29 wherein the hydrocarbyl entity is methyl, phenyl and vinyl.

31. The derivative of claim 24 wherein $R^2$ is an unsubstituted or hydrocarbylsiloxy substituted hydrocarbyl silyl group.

32. The derivative of claim 31 wherein the hydrocarbyl entity is methyl, phenyl and vinyl.

* * * * *